United States Patent [19]

Rauscher et al.

[11] Patent Number: 4,818,692
[45] Date of Patent: Apr. 4, 1989

[54] METHOD AND REAGENT COMPOSITIONS FOR DETERMINING ALPHA AMYLASE USING A BLOCKED AND LABELED SUBSTRATE

[75] Inventors: Elli Rauscher, Munich; Eugen Schaich, Weilheim; Ulrich Neumann, Peissenberg; August Wahlefeld, Hohenpeissenberg; Wolfgang Gruber, Tutzing-Unterzeismering; Bernhard Empl, Weilheim, all of Fed. Rep. of Germany

[73] Assignee: Boehringer Mannheim GmbH, Mannheim, Fed. Rep. of Germany

[21] Appl. No.: 68,612

[22] Filed: Jul. 1, 1987

Related U.S. Application Data

[62] Division of Ser. No. 637,517, Aug. 3, 1984, Pat. No. 4,709,020.

[30] Foreign Application Priority Data

Aug. 8, 1983 [DE] Fed. Rep. of Germany ....... 3328616

[51] Int. Cl.⁴ .......................... C12Q 1/34; C12Q 1/40
[52] U.S. Cl. ........................................ 435/18; 435/22; 435/810
[58] Field of Search ............................. 435/22, 810, 18

[56] References Cited

U.S. PATENT DOCUMENTS

| | | | | |
|---|---|---|---|---|
| 4,102,747 | 7/1978 | Driscoll et al. | ......................... | 435/22 |
| 4,233,403 | 11/1980 | Menson et al. | ......................... | 435/22 |
| 4,550,077 | 7/1981 | Woodbridge | ......................... | 435/22 |
| 4,622,295 | 11/1986 | Ikenaka et al. | ......................... | 435/22 |
| 4,649,108 | 3/1987 | Blair | ......................... | 435/22 |

FOREIGN PATENT DOCUMENTS

| | | | | |
|---|---|---|---|---|
| 59-31699 | 2/1984 | Japan | ......................... | 435/22 |
| 60-87297 | 5/1985 | Japan | ......................... | 435/22 |
| 237998 | 10/1985 | Japan | ......................... | 435/22 |

OTHER PUBLICATIONS

Laeseche et al., Liebigs Ann. Chem., 11, 1910–1919 (1983).
Green, in Whistler & Wolferen (eds). Methods in Carbohydrate Chemistry, vol. 2 (Academic Press, N.Y. 1963).
Matsui et al., "Research of Reactivity and Hydrolysis Type on Various Substrates for alpha Amylase Assay by HPLC", Japan Clinical Chemistry Association Summer Seminar (Jul. 1982).
Marshall: Anal. Biochem. 85: 541–549 (1978).
Marshall et al.: Clin. Chim. Acta 76: 277–283 (1977).
Biomedix, "Amylase U.V. Delta Test Assay" (Becton Dickinson, 1980).

Primary Examiner—Esther M. Kepplinger
Attorney, Agent, or Firm—Felfe & Lynch

[57] ABSTRACT

The present invention provides compounds of the general formula:

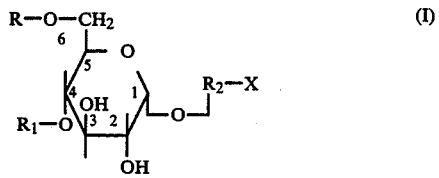

in which R and $R_1$, independently of one another, each represent a straight-chained or branched alkyl or alkoyl radical containing up to 6 carbon atoms or a phenyl radical or R and $R_1$ together also form a methylene bridge, the hydrogen atoms of which, independently of one another, can each be substituted by an alkyl radical containing up to 5 carbon atoms or a phenyl radical, $R_2$ represents an oligoglucoside residue containing 2 to 7 glucose units and X is a hydrogen atom or an optically-determinable residue.

The present invention also provides a process for the preparation of these compounds.

31 Claims, No Drawings

METHOD AND REAGENT COMPOSITIONS FOR DETERMINING ALPHA AMYLASE USING A BLOCKED AND LABELED SUBSTRATE

This application is a divisional of Ser. No. 637,517, filed Aug. 3, 1984, now U.S. Pat. No. 4,709,020.

The present invention is concerned with new heptaose compounds and with the preparation thereof, as well as with the use thereof as substrates for the determination of α-amylase.

The determination of the α-amylase level in serum is an important clinical parameter for the pancreas function. The commercially-available reagents for the determination of α-amylase were previously preponderantly based on the use of starch or starch derivatives as substrates. However, these substrates have proved to be unsatisfactory, especially with regard to their uniformity. In order to overcome this disadvantage, starch and starch derivatives have been replaced by oligosaccharides and optically-determinable derivatives thereof, maltotetraose, -pentaose, -hexaose and -heptaose and derivatives thereof having, in particular, provided interesting improvements (see published Federal Republic of Germany Patent Applications Nos. 27 41 192 and 27 55 803 and U.S. Pat. Nos. 3,879,263 and 4,000,042).

An especially interesting embodiment of the α-amylase determination with the use of the said oligoglucosides is provided in the presence of α-glucosidase since a complete breakdown of the oligoglucoside to glucose can hereby be achieved and the glucose can then be easily determined by means of processes known for this purpose (cf. published Federal Republic of Germany Patent Application No. 27 41 192).

However, it has been found that the adjuvant enzyme α-glucosidase reduces the storage life of the finished reagent mixture since, even without the action of the α-amylase, it brings about a certain splitting of the oligoglucoside.

Therefore, it is an object of the present invention to overcome this disadvantage and to provide an α-amylase substrate which is also sufficiently storage-stable in the presence of α-glucosidase and improves the correctness of the α-amylase detection.

Thus, according to the present invention, there are provided compounds of the general formula:

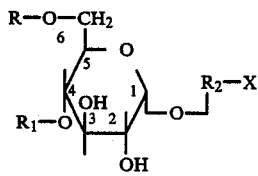
(I)

in which R and $R_1$, independently of one another, each represent a straight-chained or branched alkyl or alkoyl radical containing up to 6 carbon atoms or a phenyl radical or R and $R_1$ together also form a methylene bridge, the hydrogen atoms of which, independently of one another, can each be substituted by an alkyl radical containing up to 5 carbon atoms or a phenyl radical, $R_2$ represents an oligoglucoside residue containing 2 to 7 glucose units and X is a hydrogen atom or an optically-determinable residue, especially a nitrophenyl radical.

We have found that, with the compounds according to the present invention, the reagent ready for use, even in the presence of α-glucosidase, does not undergo any changes and, therefore, even after a long time, provides correct α-amylase values.

Examples of alkyl radicals in the compounds (I) include methyl, ethyl, n-propyl, isopropyl, n-butyl, isobutyl, t-butyl, n-pentyl, its isomers, n-hexyl, its isomers, as well as the cyclohexyl radical. In the same way, when the substituents on the oxygen atoms in the 4- and/or 6-positions of the terminal glucoside residue are alkoyl radicals, these preferably correspond to the above alkyl radicals. Preferred compounds according to the present invention are those in which R and $R_1$ together form an optionally substituted methylene bridge and especially preferred are those which are substituted by an alkyl or phenyl radical, an ethylidene or benzylidene radical being particularly preferred.

Of the oligoglucoside residues $R_2$, those are preferred which contain 3, 4 and 6 glucose units.

If X is an optically-determinable residue, it can be a residue which itself displays a colour in the visible or in the UV range or a residue which becomes optically determinable by reaction with a further compound, for example by conversion into a coloured material or by coupling with a coloured material. Such optically-determinable residues are known and do not here require any further explanation. Nitro group-containing phenyl radicals, such as nitrophenyl or 3,4-dinitrophenyl radicals, are preferred.

The preparation of the compounds according to the present invention can take place starting from oligoglucosides containing 3 to 8 glucose units which terminally optionally carry an optically-determinable group X, wherein these are reacted under esterification or etherification conditions with an orthooxy compound, preferably with a dialkoxyethane or a corresponding benzyl derivative, the formation of a compound of general formula (I), in which R and $R_1$ together form an optionally substituted methylene radical and possibly subsequently free hydroxyl groups are blocked, for example by peracetylation, the methylene bridge is split at the oxygen atom in 4- or 6-position and, if necessary, the free hydroxyl group thus formed in the 4- or 6-position is again etherified or esterified or the product is transetherified or transesterified and other hydroxyl-blocking groups, for example acetyl radicals, are subsequently split off.

The compounds with an optionally substituted methylene bridge arising as intermediate products in the case of this synthesis but otherwise also preferred as end products can, according to the present invention, be prepared by reacting a compound of the general formula:

(II)

in which X has the above-given meaning and $R_3$ is an oligoglucoside residue containing 3 to 8 glucose units, in the presence of p-toluenesulphonic acid with a compound of the general formula:

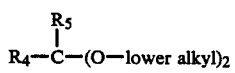
(III)

in which $R_4$ and $R_5$, independently of one another, each signifies a hydrogen atom or an alkyl radical containing up to 5 carbon atoms or a phenyl radical, in a polar organic solvent.

The polar organic solvent used is preferably dimethylformamide or formamide but other polar organic solvents with a comparable basicity can also be used.

Surprisingly, the reaction gives rise to uniform products without the numerous hydroxyl groups present having to be protected. Possibly formed byproducts can be separated off without difficulty.

The reaction is preferably carried out at a temperature of from about 10° to about 70° C., ambient temperature being especially preferred. Since byproducts are scarcely formed by the reaction, for the achievement of the best yields, it is preferable to use a stoichiometric excess of the compound of general formula (III).

Examples of compounds of general formula (III) include dimethoxymethane, dimethoxyethane, diethoxyethane, dipropoxyethane, dibutoxyethane, dimethoxypropane, dimethoxyisopropane and phenyldimethoxymethane.

Examples of compounds of general formula (II) include maltotetraose, maltopentaose, maltohexaose, maltoheptaose and the derivatives thereof terminally substituted by an optically-determinable group, such as mononitrophenylmaltoheptaose, 3,4-dinitrophenylmaltoheptaose and the like.

The superior storage stability of the compounds according to the present invention is shown by the fact that under the conditions of a widely used, commercially available α-amylase colour test with p-nitrophenylmaltoheptaoside as substrate (G7pNP) namely: buffer pH 7.1; sodium chloride 50 mM; about 30 U/ml. α-glucosidase; and 5 mM substrate, in the case of practically identical courses of reaction with regard to lag phase and linearity, with 4,6-ethylidene-p-nitrophenyl-maltoheptaoside (Eth-G7pNP), within the course of 4 days at 25° C., practically no glucose is formed, whereas with G7pNP, a noticeable splitting to glucose takes place. Under the same conditions at 4° C., with the substrate according to the present invention, after 8 days there is no glucose formation but in the case of the comparison substrate, a noticeable splitting occurs. Therefore, according to the present invention, new compounds are provided which, as substrates for α-amylase in the presence of α-glucosidase, display superior properties.

The following Examples are given for the purpose of illustrating the present invention:

EXAMPLE 1

Process for the preparation of 4,6-ethylidene-4-nitrophenyl-α-D-maltoheptaoside

Batch:
250 g. (196 mMol) 4-nitrophenyl-α-D-maltoheptaoside
31.5 ml. (297 mMol) acetaldehyde dimethylacetal
20 g. p-toluenesulphonic acid monohydrate
1.5 liters dimethylformamide (DMF)

Synthesis:

250 g. 4-nitro-α-D-maltoheptaoside and 20 g. p-toluenesulphonic acid monohydrate are dissolved in about 1.5 liters DMF and, for rendering anhydrous, are evaporated to dryness on a rotary evaporator, the water content thereby decreasing from 0.4% to 0.02%.

The residue is dissolved in 1.5 liters DMF, 31.5 ml. acetaldehyde dimethyl acetal are added thereto and the reaction mixture is first stirred at 50° C. for 9 hours and then maintained for about 10 hours at ambient temperature. The reaction mixture is evaporated to dryness and the residue is dissolved in water, adjusted with lithium hydroxide solution to pH 7.3, clarified by filtration and evaporated to 750 ml.

The HPLC analysis of the product shows a content of about 75 to 80% of ethylidene-4-nitrophenyl-α-D-maltoheptaoside with about 20% of starting material.

Chromomatographic purification:

The sample solution (750 ml.) is applied to a 150×25 cm. column with 70 liters "Dowex" 50 WX2 (200 to 400 mesh) lithium+ and eluted with water at a flow rate of 1.5 liters/hour. 4.5 liter fractions are thereby collected, the chromatography being monitored by means of a UV detector at 280 nm.

After about 100 liters, unreacted 4-nitrophenyl-α-D-maltoheptaoside is eluted and after about 200 liters the disired product is eluted.

The fractions which contain the desired product are combined and evaporated to dryness. The residue is dissolved in 1.5 liters methanol, filtered and precipitated at 0° C. with 4 liters isopropanol and 10 liters petroleum ether. After stirring overnight at 4° C., the product is filtered off with suction, washed with isopropanol and petroleum ether and dried at 30° C. in a drying cabinet.

Yield: 150 g. (58of theory) of colourless powder.
Molecular weight 1300.
Water content (according to K. Fischer) 4.5%.
Isopropanol (gas chromatographically) 5%.
Acetaldehyde after acidic hydrolysis (enzym.) 91%.
$[\alpha]_D^{25}$ referred to dry substance=77° (c=1, $H_2O$).
HPLC: 99 surface percent (5 $\mu$-$NH_2$ column; acetonitrile/water 1:1 v/v, 1 mMol/l c-phosphoric acid, detection at 305 nm).

EXAMPLE 2

Process for the preparation of 4,6-ethylidenemaltoheptaose

Batch:
10 g. (8.7 mMol) Maltoheptaose
1.8 ml. (17 mMol) acetaldehyde dimethyl acetal
1 g. p-toluenesulphonic acid monohydrate
75 ml. DMF Synthesis:

10 g. Maltoheptaose and 1 g. p-toluenesulphonic acid monohydrate are dissolved in 100 ml. DMF and evaporated to dryness. In this way, the residue is freed from water. The residue is dissolved in 75 ml. DMF, mixed with 1.7 ml. acetaldehyde dimethyl acetal and stirred for 15 hours in a closed vessel at 50° C. The reaction solution is then evaporated to dryness and the residue is dissolved in water, neutralised with lithium hydroxide to pH 7, filtered clear and concentrated to 50 ml.

Chromatographic purification:

The 50 ml. sample solutions are applied to a chromatography column (180×5 cm.) with 3.5 liters "Dowex" 50 WX2 (200 to 400 mesh) Li+ and eluted with water at a flow rate of 150 ml./hour. 30 ml. fractions are collected which run through a UV detector (280 nm).

After 1.8 liters, maltoheptaose is eluted and after 2.25 liters maltoheptaose is eluted.

The main fractions are combined and evaporated to dryness in a rotary evaporator. The residue is dissolved in 200 ml. methanol with the addition of some water, mixed with 200 ml. isopropanol and stirred at 4° C., the product thereby precipitating out. It is filtered off with suction, washed with isopropanol and petroleum ether and dried in a vacuum at 25° C. over phosphorus pentoxide.

Yield: 6.2 g. (60% of theory).

Analysis: water content (according to K. Fischer) 7.6%.

Acetaldehyde after acidic hydrolysis (enzym.) 91.2%.

$[\alpha]_D^{25}$ referred to dry substance (c=1, H₂O)=69°.

HPLC (conditions see Example 1): 96 surface percent.

The reaction with tetrazolium blue demonstrates that the reducing end is free.

EXAMPLE 3

Reagent: 682.5 mg. ethylidene-G₇PNP (5.25 mMol/liter) are dissolved in 100 ml. sodium phosphate buffer (105 mMol/liter), containing sodium chloride (52.5 mMol/liter), as well as α-glucosidase (42 U/ml.), and adjusted to pH 7.10.

End concentration in the test: phosphate buffer 100 mMol/liter, sodium chloride 50 mMol/liter, substrates 5 mMol/liter, α-glucosidase 40 U/ml. Test batch: To 2.0 ml. of reagent tempered to 25° C. are added 0.1 ml. of sample and the mixture is tempered to 25° C. After a pre-incubation time of 4 minutes (lag phase), the extinction increase at Hg 405 nm is registered with a recorder on an Eppendorf photometer. From the extinction change per minute (αE/min.) is calculated the activity of the amylase in the samples according to the following formula:

$$\frac{\Delta E/\min \cdot V \cdot 1000 \cdot 3}{E \cdot v \cdot d} = \Delta E/\min \cdot 7000[U/L]$$

Finding again of α-amylase: The determination of the activity is repeated with reagent stored at 4° C. and at 25° C. for definite intervals of time, the following values being found:

| storage of the reagent | human serum 1 U/l. | human serum 2 U/l. | control serum PNU 572 U/l. |
|---|---|---|---|
| starting value | 118 | 383 | 214 |
| 4 hours at 25° C. | 120 | 379 | 214 |
| 8 hours at 25° C. | 120 | 391 | 216 |
| 24 hours at 25° C. | 113 | 360 | 209 |
| 32 hours at 25° C. | 120 | 392 | 217 |
| 48 hours at 25° C. | 126 | 382 | 214 |
| 8 hours at 4° C. | 119 | 370 | 210 |
| 24 hours at 4° C. | 118 | 387 | 215 |
| 48 hours at 4° C. | 123 | 393 | 208 |
| 72 hours at 4° C. | 113 | 401 | 223 |
| 80 hours at 4° C. | 121 | 375 | 219 |
| average value/VK | 119 3.2% | 383 3.0% | 214 2.0% |

The individual values lie within the usual variation breadth for manual determinations of enzyme activities.

We claim:

1. Method for determining alpha amylase in a sample comprising adding to said sample a compound of the formula:

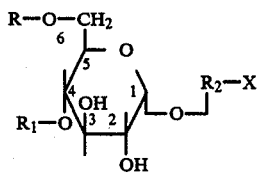
(I)

in which R and R₁, independently of one another, each represent a straight-chained or branched alkyl or alkoyl radical containing from 1 to 6 carbon atoms or a phenyl radical or R and R₁ together form a methylene bridge, the hydrogen atoms of which, independently of one another, can each be substituted by an alkyl radical containing from 1 to 5 carbon atoms or a phenyl radical, R₂ represents an oligoglucoside residue containing 2 to 7 glucose units and X is a hydrogen or an optically-determinable residue, in the presence of alpha glucosidase; and determining X as a measure of the presence or absence or amount of alpha amylase in said sample.

2. Method as in claim 1, wherein X is nitrophenyl.

3. Method as in claim 1, wherein X is 3,4-dinitrophenyl.

4. Method as in claim 1, wherein X is hydrogen.

5. Method as in claim 1, wherein R and R₁ form a methylene bridge substituted by a methyl radical to form ethylidene.

6. Method as in claim 5, wherein X is a nitrophenyl.

7. Method of claim 5, wherein R₂ represents an oligoglucoside residue containing 6 glucose units.

8. Method as in claim 1, wherein R and R₁ form a methylene bridge substituted by a phenyl radical to form benzylidene.

9. Method of claim 8, wherein R₂ represents an oligoglucoside residue containing 6 glucose units.

10. Method of claim 1, wherein at least one of R and R₁ is an alkyl radical of from 1 to 6 carbon atoms.

11. Method of claim 10, wherein said alkyl radical is selected from the group consisting of methyl, ethyl, n-propyl, isopropyl, n-butyl, isobutyl, t-butyl, n-pentyl and its isomers, n-hexyl and its isomers and cyclohexyl.

12. Method of claim 1, wherein at least one of R and R₁ is an alkoyl radical of from 1 to 6 carbon atoms.

13. Method of claim 12, wherein said alkoyl radical is a derivative of an alkyl selected from the group consisting of methyl, ethyl, n-propyl, isopropyl, n-butyl, isobutyl, t-butyl, n-pentyl and its isomers, n-hexyl and its isomers and cyclohexyl.

14. Method of claim 1, wherein at least one of R and R₁ is a phenyl radical.

15. Method of claim 1, wherein R and R₁ form a methylene bridge.

16. Method of claim 15, wherein said methylene bridge is substituted by an alkyl radical of from 1 to 5 carbon atoms or a phenyl radical.

17. Method of claim 1, wherein R₂ contains 3, 4 or 6 glucose residues.

18. Method of claim 1, wherein said compound is 4,6-ethylidene-4-nitrophenyl-alpha-D-maltoheptaoside.

19. Method of claim 1, wherein said compound is 4,6-ethylidene maltoheptaoside.

20. Method of claim 1, wherein R₂ represents an oligoglucoside residue containing 6 glucose units.

21. Reagent for determination of alpha amylase comprising a compound of the formula:

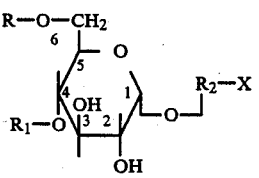
(I)

in which R and R₁, independently of one another, each represent a straight-chained or branched alkyl or alkoyl radical containing from 1 to 6 carbon atoms or a phenyl radical or R and $R_1$ together form a methylene bridge, the hydrogen atoms of which, independently of one another, can each be substituted by an alkyl radical containing from 1 to 5 carbon atoms or a phenyl radical, $R_2$ represents an oligoglucoside residue containing 2 to 7 glucose units and X is a hydrogen or an optically-determinable residue; and alpha glucosidase.

22. Reagent of claim 21, wherein X is nitrophenyl.

23. Reagent of claim 21, wherein X is 3,4-dinitrophenyl.

24. Reagent of claim 21, wherein R and $R_1$ form a methylene bridge substituted by a methyl radical to form ethylidene.

25. Reagent of claim 24, wherein $R_2$ represents an oligoglucoside residue containing 6 glucose units.

26. Reagent of claim 21, wherein R and $R_1$ form a methylene bridge substituted by a phenyl radical to form benzylidene.

27. Reagent of claim 26, wherein $R_2$ represents an oligoglucoside residue containing 6 glucose units.

28. Reagent of claim 21, wherein $R_2$ contains 3, 4, or 6 glucose residues.

29. Reagent of claim 21, wherein said compound is 4,6-ethylidene-4-nitrophenyl-alpha-D-maltoheptaoside.

30. Reagent of claim 21, wherein said compound is 4,6-ethylidene maltoheptaoside.

31. Reagent of claim 21, wherein $R_2$ represents an oligoglucoside residue containing 6 glucose units.

* * * * *